United States Patent [19]

Frisch

[11] 4,100,246
[45] Jul. 11, 1978

[54] METHOD OF FORMING A GASTROINTESTINAL TUBE

[75] Inventor: Eldon E. Frisch, Midland, Mich.

[73] Assignee: Dow Corning Corporation, Midland, Mich.

[21] Appl. No.: 698,396

[22] Filed: Jun. 21, 1976

[51] Int. Cl.² .............................................. B29C 13/00
[52] U.S. Cl. ................................ 264/230; 128/349 B; 128/350 R; 128/351; 264/150; 264/209; 264/234; 264/249; 264/342 R; 264/343; 264/DIG. 71
[58] Field of Search ............... 264/150, 209, 230, 342, 264/343, DIG. 71, 234, 249; 128/349 B, 349 BV, 350 R, 351

[56] References Cited

U.S. PATENT DOCUMENTS

| | | | |
|---|---|---|---|
| 3,544,672 | 12/1970 | Goda | 264/230 |
| 3,634,924 | 1/1972 | Blake | 264/230 X |
| 3,755,525 | 8/1973 | Sheridan | 264/209 X |
| 3,833,004 | 9/1974 | Vasquez | 264/230 X |
| 3,972,548 | 8/1976 | Roseen | 264/DIG. 71 |
| 3,975,039 | 8/1976 | Penneck | 264/230 X |

Primary Examiner—Thomas P. Pavelko
Attorney, Agent, or Firm—Howard W. Hermann

[57] ABSTRACT

In accordance with a preferred embodiment of this invention, there is provided a new and improved method of forming a four-lumen gastrointestinal tube. This tube may be characterized as having two lumens which extend nearly the full length of the tube and two lumens which extend through only a portion of the tube. The subject method comprises the steps of: (1) extruding a three-lumen sleeve portion wherein one of the lumens is an insert carrying lumen and the remaining two lumens, in the final gastrointestinal tube assembly, are those lumens which extend the full length of the tube; (2) extruding a two-lumen insert portion, the lumens of which in the final gastrointestinal tube assembly, extend the full length of the assembly, and wherein the external dimensions of the insert portion are slightly larger than the internal dimensions of the insert carrying lumen of the sleeve portion; (3) immersing the sleeve portion in a solvent, preferably chlorothene, to cause it to swell until the internal dimensions of the insert carrying lumen are slightly larger than the external dimensions of the two-lumen insert portion; (4) inserting the insert portion into the insert carrying lumen; and (5) removing the solvent and thereby causing the insert carrying lumen in the sleeve portion to contract around the insert portion forming a "solvent shrink fit."

1 Claim, 4 Drawing Figures

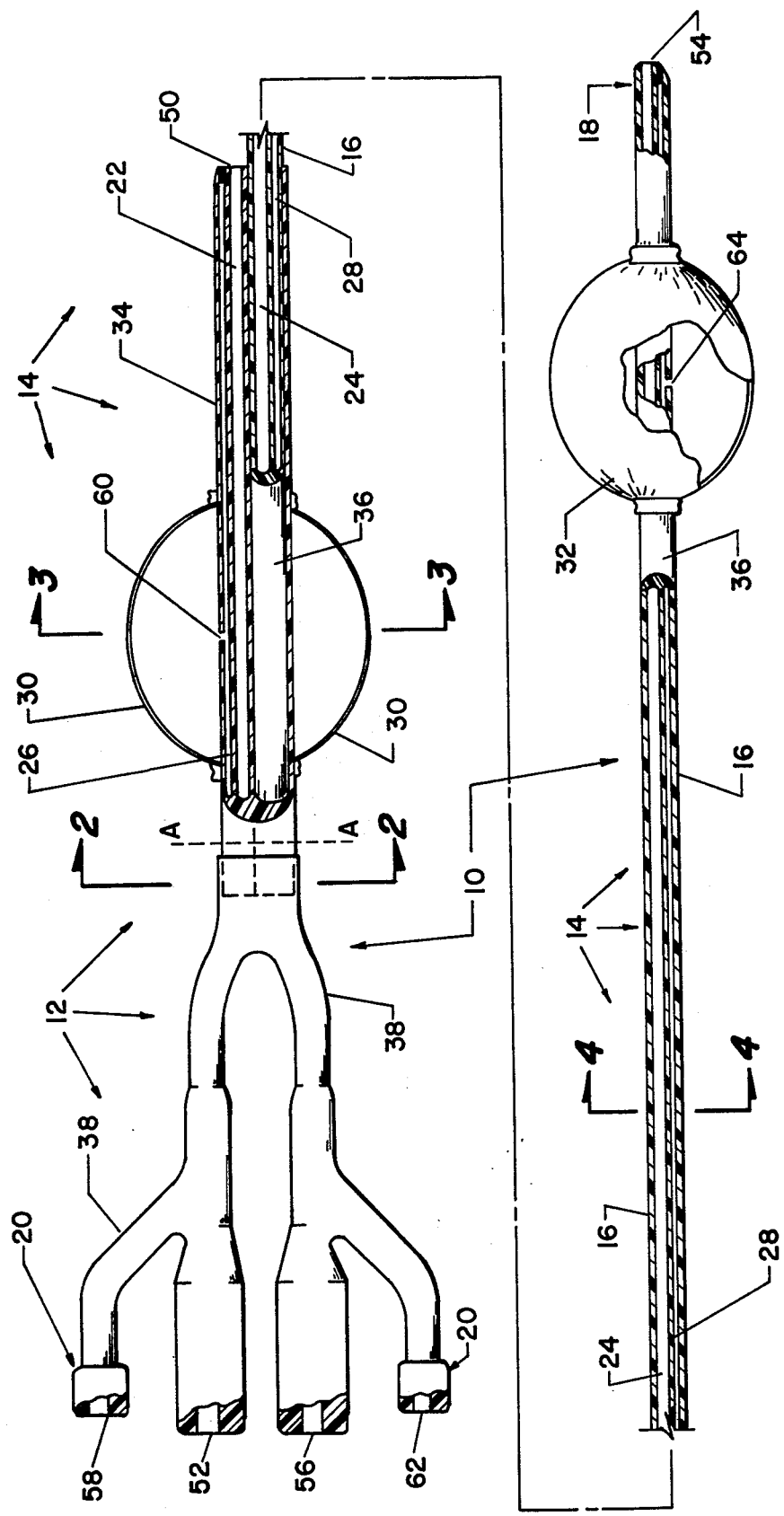
FIG. I

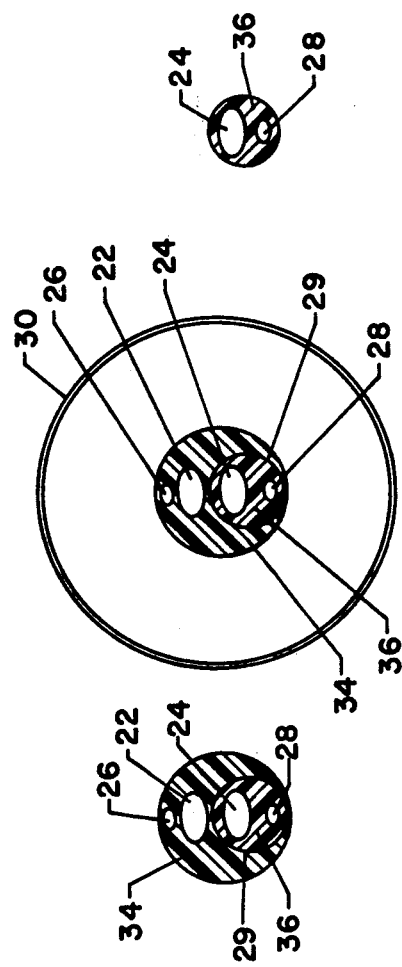

METHOD OF FORMING A GASTROINTESTINAL TUBE

FIELD OF THE INVENTION

This invention relates to a method of forming a multi-lumen gastrointestinal tube having lumens of unequal length.

BACKGROUND OF THE INVENTION

This invention provides a method of forming an improved multi-lumen gastrointestinal tube which may be surgically inserted into a patient's stomach and then threaded downward into the intestine to provide both intestinal stent plication and independently controllable gastric and intestinal decompression. The subject tube comprises a proximal portion which remains external to the patient's body and a distal portion which remains inside the patient's body for a period of up to two weeks during the post-operative healing process. There are preferably four separate lumens in the proximal portion of the subject tube and these lumens extend from the proximal (external) end of the tube into the patient's body. Two of the lumens terminate in the stomach and the other two lumens extend the full length of the subject tube.

The manufacture of any elongated multi-lumen vulcanized elastomeric member having lumens of unequal length is cumbersome and the production costs are correspondingly high. A primary problem is that elongated elastomeric members or tubes are typically made by extrusion processes and these processes are not readily adapted to form members having an abrupt and complex change in any cross-sectional dimension.

SUMMARY OF THE INVENTION

This invention provides an improved and economical method of producing a multi-lumen percutaneous gastrointestinal tube adapted to provide independently controllable decompression to the stomach and to the intestine. This tube may be characterized as having lumens of unequal lengths and an abrupt change in its cross-sectional dimensions.

In accordance with a preferred embodiment of this invention the subject gastrointestinal tube is formed by first separately forming a two-lumen tube (insert portion) and a three-lumen tube (sleeve portion). These tubes are eventually assembled by securing the insert portion in one lumen, termed the insert carrying lumen, of the sleeve portion and thereby forming the desired four-lumen tube. When this assembly is properly placed in the patient's body the sleeve portion extends from outside the patient's body into the stomach. The two "open" lumens (i.e., the two non-insert carrying lumens) of the sleeve portion tube provide means to inflate and deflate an inflatable cuff located in the stomach at the inner surface of the incision and means to decompress (i.e., to withdraw fluids from) the stomach. In addition, the sleeve portion carries the insert portion through the incision and into the stomach. The insert portion extends from the sleeve portion down into the intestine to provide intestinal stent plication and intestinal decompression. One of the two lumens which extend the length of the insert portion is vented into an inflatable cuff which is located at or near the distal end (that end which is inside the patient's body) of the insert portion; this lumen provides means to inflate and deflate this cuff. The remaining lumen is vented at the distal end and provides means to decompress the intestine.

The internal dimensions of the insert carrying lumen in the sleeve portion are slightly smaller, preferably by from about 5 to 10 percent, than the external dimensions of the insert portion. However, prior to assembly the sleeve portion is immersed in a solvent, preferably chlorothene, (methyl chloroform) to swell the sleeve portion and more specifically to swell the insert carrying lumen to a point where the insert portion may be easily inserted therein. The solvent is then removed causing the insert carrying lumen to contract around the insert portion forming a "solvent shrink fit" and securely fixing the insert portion in the insert carrying lumen. Preferably, the proximal end (that end which remains external to the patient's body) of the insert portion is flush or nearly so with the proximal end of the sleeve portion.

An end piece, which is preferably a molded product, is securely attached to the proximal end of the subject four-lumen composite tube. This end piece provides independently controllable access to each of the four lumens.

These and other features, objects and advantages of the subject invention will be more readily understood in view of the following detailed description which will make reference to the attached drawings which are:

FIG. 1 is an elevated cut-away view of a preferred embodiment of the subject percutaneous gastrointestinal tube with both cuffs inflated;

FIG. 2 is a cross-sectional view of the subject percutaneous gastrointestinal tube taken at section 2—2 of FIG. 1;

FIG. 3 is a cross-sectional view of the subject percutaneous gastrointestinal tube taken at section 3—3 of FIG. 1; and FIG. 4 is a cross-sectional view of the subject percutaneous gastrointestinal tube taken at section 4—4 of FIG. 1.

This invention provides a method of forming a percutaneous gastrointestinal tube 10 having an elongated, smooth surfaced, member 16, preferably formed of a soft flexible elastomer, and an end piece 38. The subject tube 10 should be formed from a material which is able to withstand a thorough cleaning and sterilization and also should be compatible with, that is cause no significant irritation to, human body tissue after contact therewith for a period of up to several weeks or more. In addition, the material must be capable of swelling when immersed in a solvent or treated in some other manner and then returning to its original shape; this criterium applied only to the material used to form the sleeve portion 34. The compatibility criteria may be met by either forming the subject tube 10 from a base elastomer which is, itself, compatible with the human body or coating a tube with a compatible material. Suitable elastomeric materials which may be compatible with the human body, if the formulations are controlled so as to avoid harmful additives, include vulcanized gum rubber, silicone rubber, butyl rubber, natural rubber, butadiene-styrene copolymers, and the like. However, the particular base elastomer is not critical to the subject invention and the above are included as merely illustrative and not limiting examples.

With reference to the aforementioned coating technique, the subject tube 10 may be formed of a silicone rubber coated elastomer such as that described and fully disclosed in U.S. Pat. No. 3,434,869. This patent is hereby incorporated by reference to illustrate that particular silicone rubber coated elastomeric structure.

The subject tube 10 may be viewed as having two portions; an upper proximal portion 12, (See FIG. 1) which remains external to the patient's body during use and a lower distal portion 14 which is inside the patient's body once the subject tube 10 is in place. Line A—A indicates the approximate position on the subject tube 10 of the incision when the subject tube 10 is properly placed in the patient's body and therefore represents the dividing line between the proximal portion 12 and the distal portion 14. Preferably, the subject tube 10 will have an outside diameter of about one quarter of an inch. However, the exact dimensions of the subject tube 10 are not critical to this invention, as long as the distal portion 14 will readily fit inside the intestinal lumen.

During any surgical procedure which indicates either intestinal stent plication, or decompression of the stomach and/or the intestine, or both, the distal portion 14 of the subject tube 10 may, after being suitably cleaned and sterilized, be surgically inserted into the patient's stomach and then threaded downward into the intestine. The presence of the elongated elastomeric distal portion 14 of the subject tube 10 will ensure that the intestine will remain in a gently curving configuration during the healing process. Therefore, as the patient recovers, there will be little danger of adhesions obstructing or crimping the intestinal lumen because there will be no sharp curves or kinks in the intestine (this is termed intestinal stent plication). In addition, it is to be noted that the subject tube 10 may be extended to plicate and/or decompress the colon.

To provide either or both gastric and intestinal decompression, the subject tube 10 has two decompression lumens; a stomach decompression lumen 22 (See FIGS. 1, 2, and 3) which extends through the proximal portion 12 and the upper portion of the distal portion 14 and is vented in the stomach and an intestinal decompression lumen 24, which extends the entire length of the subject tube 10 and is vented at or near the distal end 18. More specifically, the stomach decompression lumen 22 provides independently controllable fluid communication between a distal stomach decompression lumen opening 50 which will be in the patient's stomach when the subject tube 10 is in place, and a proximal stomach decompression lumen opening 52 in the proximal end 20 of the subject tube 10. This communication provides a means to withdraw or insert either or both liquids and gases from the patient's stomach. Typically, fluids are withdrawn to relive stress on the stomach and ensure that no undue pressure will be placed on the stomach wall. This is particularly important if an incision has been made in the stomach wall since such pressure may post-operatively rupture or re-open this incision. In addition, by removing the excess gases and liquids from the stomach, they are not passed through to stress the lower gastrointestinal tract.

Similarly, the intestinal decompression lumen 24 provides fluid communication between a distal intestinal decompression lumen opening 54 in the distal end 18 of the subject tube 10 and a proximal intestinal decompression lumen opening 56 in the proximal end 20 of the subject tube 10. The intestinal lumen 24 is primarily used to withdraw liquids and gases, that is to decompress, the patient's intestine and/or colon. This intestinal decompression procedure is particularly useful as the surgeon is threading the subject tube 10 downward from the patient's stomach into the intestine since the slightly lower pressure ahead of the distal end 18 helps to pull the tube 10 through the intestinal lumen.

As shown in FIGS. 2, 3 and 4 the decompression lumens have an oval shape and are about one hundred mils wide. However, it is to be understood that the exact size and shape of the lumens, to include both the decompression and the inflation-deflation lumens, is not critical to the practice of this invention. The size and shape of all lumens may, within limits, be dictated by processing or material factors; the primary limit is that the size and shape should be adequate to provide the desired fluid communication. A problem to be noted is that as the size of the lumens decrease, the lumens may be crimped and thereby closed by the curves which the subject tube 10 will assume in the patient's body.

The distal portion 14 of the subject tube 10 is provided with two, fixed and thin walled, inflatable cuffs—-an upper inflatable cuff 30 and a lower inflatable cuff 32. The upper inflatable cuff 30 is positioned near the proximal portion 12, and is typically inflated after the subject device has been inserted and positioned in the patient's body. After the upper inflatable cuff 30 is inflated, it is positioned against the inner surface of the stomach wall at the incision.

The lower inflatable cuff 32 is positioned near the distal end 18 of the subject tube 10 and is preferably inflated after the distal end 18 of the subject tube 10 and the lower inflatable cuff 32 have been inserted through the stomach and passed through the pyloris, jejunum, and the ligament of Treitz. Once the lower inflatable cuff 32 is inflated, typically with water to provide a firm balloon, the surgeon is able to manually control the distal end 18 of the subject tube 10 through the intestinal wall 46 and quickly thread it downward as far as necessary.

An upper cuff inflation-deflation lumen 26 provides fluid communication between a proximal upper cuff lumen opening 58 in the proximal end 20 of the subject tube 10 and the upper inflatable cuff 30 through an internal upper cuff lumen opening 60. Similarly, a lower cuff inflation-deflation lumen 28 provides fluid communication between a proximal lower cuff lumen opening 62 in the proximal end 20 of the subject tube 10, and the lower inflatable cuff 32 through an internal lower cuff lumen opening 64. It is through these inflation-deflation lumens 26 and 28, that the surgeon may independently inflate and deflate the cuffs 30 and 32. Preferably, there are valves (not shown) located in the proximal end 20 in each cuff lumen to provide a means of controlling the flow fluids. If desired, valves may be included in the other lumens as well. The particular valve and its internal mechanism is not critical to the subject invention and any valve known in the art which could readily be attached to the subject tube 10 and adequately provide the necessary opening and sealing functions would be suitable.

In accordance with the practice of this invention, the subject gastrointestinal tube is formed in three sections: a sleeve section 34, an insert section 36, and an end piece 38. The sleeve section 34 and the insert section 36 are preferably extruded products since they have constant cross-sectional dimensions. Any of the well known extrusion processes used to form elastomeric tubes would be suitable. The end piece 38, is preferably a molded product. As is evident from FIGS. 2 and 3, the sleeve portion 34 has three lumens, the upper cuff inflation-deflation lumen 26, the stomach decompression lumen 22, and an insert carrying lumen 29. (The lead line from the number 29 in FIGS. 2 and 3 indicates the wall of the insert carrying lumen.)

The sleeve portion 34 and the insert portion 36 are formed such that the external dimensions of the insert portion 36 are slightly larger, preferably by about 5 to 10 percent, than the internal dimensions of the insert carrying lumen 29 of the sleeve portion 36. However, the exact percentage is not critical to this invention, and may be adapted to the practitioner's processes and materials. It is to be noted at this point that the shapes of the insert portion 36 and the insert carrying lumen 29 should correspond. That is, to say, that if the insert portion 36 has a circular cross-section so should the insert carrying lumen 29; this will facilitate processing.

Prior to the assembly of the sleeve portion 34 and the insert portion 36, (that is, the insertion of the insert portion 36 into the insert carrying lumen 29) the sleeve portion 34 is immersed in a suitable solvent, which includes aromatic solvents, aliphatic solvents, chlorinated hydrocarbon solvents, ethers and esters and the like. The preferred solvents are those which do not leave a contaminate and which present no hazards in processing. The immersion step causes the sleeve portion 34 to swell and thereby increases the internal dimensions of the insert carrying lumen 29. The sleeve portion 34 is immersed until this lumen 29 is large enough to receive the insert portion 36. The two extruded portions are then assembled and the solvent is removed by any of several known drying processes. As the solvent is removed the sleeve portion 34 shrinks and the insert carrying lumen 29 contracts around the insert portion 36 forming a secure "solvent shrink fit." Preferably, the proximal ends of the insert portion 36 and of the sleeve are flush to allow easy access to each of the four lumens.

Another suitable technique of assembling the sleeve and insert portions would be to form the sleeve portion 34 from a heat shrinkable elastomer, and then heat and expand (i.e., swell) the sleeve portion 34 with air pressure and cool it in the expanded condition. The cooling step would temporarily "set" or freeze the sleeve portion 34 in its expanded shape. The insert carrying lumen would then be large enough to receive the insert portion 36 and after the insertion step, the assembly would be heated to "release" the sleeve portion and allow it to shrink back to its original shape. This process would form a "heat shrink fit."

Once the insert portion 36 and the sleeve portion 34 have been assembled, the end piece 38 may be securely attached, by the use of any of the known suitable adhesives, to the proximal end of the aforementioned assembly. It would also be suitable to use the "solvent shrink fit" technique for attaching the end piece 38 to the assembly. The end piece 38 is preferably molded by one of several well known processes including transfer molding, injection molding and the like.

While my invention has been described in terms of certain specific embodiments, it will be appreciated that other forms thereof could readily be adopted by one skilled in the art. Therefore, the scope of my invention is not to be limited to the specific embodiments disclosed.

That which is claimed is:

1. A method of forming an elastomeric four-lumen gastrointestinal tube assembly which may be surgically inserted into a patient's stomach and threaded downward into the intestine to provide both intestinal stent plication and gastric and/or intestinal decompression; said assembly having a proximal portion which remains external to the patient's body and a distal portion which is internal to the patient's body when the tube is properly placed, said method comprising the steps of:
  (a) extruding an elastomeric three-lumen sleeve portion which when the assembly is formed and placed in the patient's body extends from the proximal portion into the patient's stomach, and wherein the sleeve portion one of the lumens is an insert carrying lumen;
  (b) extruding a elastomeric two-lumen insert portion, which when the assembly is formed and placed in the patient's body extends from the proximal portion through the sleeve portion through the patient's stomach and into the intestine; the external shape of the insert portion approximating the shape of the insert carrying lumen and the external dimensions of the insert portion being larger than the internal dimensions of the insert carrying lumen;
  (c) immersing the sleeve portion in a solvent to swell the sleeve portion and to increase the internal dimensions of the insert carrying lumen until the internal dimensions are larger than the external dimensions of the insert portion;
  (d) inserting the insert portion into the insert carrying lumen, and
  (e) removing the solvent and thereby causing the sleeve portion to shrink and the insert carrying lumen to contract around the insert portion thereby forming a "solvent shrink fit" which securely fixes the insert portion in the insert carrying lumen.

* * * * *